(12) United States Patent
Ramakrishna et al.

(10) Patent No.: US 6,297,043 B1
(45) Date of Patent: Oct. 2, 2001

(54) MUMBAISTATIN, A PROCESS FOR IT'S PRODUCTION AND ITS USE AS A PHARMACEUTICAL

(75) Inventors: Nirogi Venkata Satya Ramakrishna; Keshavapura Hosamane Sreedhara Swamy; Erra Koteswara Satya Vijaya Kumar, all of Mumbai; Manoj Maniram Singh Kushwaha, Thane; Sridevi Kota, Andheri; Mythili Raman; Swati Dhananjay Tare, both of Mumbai; Sunil Kumar Deshmukh, Maharashtra, all of (IN); Dietmar Schummer, Langen (DE); Michael Kurz, Hofheim (DE); Herbert Kogler, Glashütten (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/338,601

(22) Filed: Jun. 23, 1999

(30) Foreign Application Priority Data

Jun. 24, 1998 (EP) .................................. 98111636

(51) Int. Cl.[7] .............................. C12N 1/00; C12N 1/20; C12P 1/00; C12P 33/00
(52) U.S. Cl. ..................... 435/253.5; 424/93.43; 435/41; 435/52; 435/170; 435/183; 435/252.1; 435/822; 435/886
(58) Field of Search ................. 435/252.1, 822, 435/41, 52, 170, 183, 253.5, 886; 424/93.43, 94.1

(56) References Cited

U.S. PATENT DOCUMENTS 3,905,942    9/1975    Takekoshi et al. ................ 260/47

FOREIGN PATENT DOCUMENTS 24 29 648    1/1975    (DE) .

OTHER PUBLICATIONS

Chemical Abstract No. 112467, vol. 113, No. 13 (Sep. 24, 1990).
Chemical Abstract No. 18102, vol. 110, No. 3 (Jan. 16, 1989).
Chemical Abstract No. 233720, vol. 118, No. 23 (Jun. 7, 1993).
Chemical Abstract No. 164483, vol. 108, No. 19 (May 9, 1988).
Chemical Abstract No. 91433, vol. 108, No. 11 (Mar. 14, 1988).
Chemical Abstract No. 179247, vol. 98, No. 21 (May 23, 1983).
Chemical Abstract No. 50979, vol. 108, No. 7 (Feb. 15, 1988).
Chemical Abstract No. 33313, vol. 103, No. 5 (Aug. 5, 1985).
Chemical Abstract No. 99360, vol. 94, No. 13 (Mar. 30, 1981).
Chemical Abstract No. 90000, vol. 72, No. 17 (Apr. 27, 1970).
International Search Report, dated Sep. 20, 1999.

*Primary Examiner*—Deborah K. Ware
(74) *Attorney, Agent, or Firm*—Finnegan, Henderson, Farabow, Garrett and Dunner, L.L.P.

(57) ABSTRACT

The present invention relates to a compound named Mumbaistatin, its pharmaceutically acceptable salts and derivatives, a process for its production, and its use as a pharmaceutical. Mumbaistatin is obtainable by cultivation of the microorganism HIL-008003 (DSM 11641). Mumbaistatin is a glucose-6-phosphate translocase inhibitor and can be used in the treatment of diabetes mellitus. The present invention further relates to a process for the production of Mumbaistatin, to the microorganism HIL-008003 (DSM 11641), to the use of Mumbaistatin and its pharmaceutically acceptable salts and derivatives as pharmaceuticals, in particular to their use in the treatment of diabetes mellitus, and to pharmaceutical compositions comprising Mumbaistatin or a pharmaceutically acceptable salt or derivative thereof.

13 Claims, 10 Drawing Sheets

MUMBAISTATIN, A PROCESS FOR IT'S PRODUCTION AND ITS USE AS A PHARMACEUTICAL

The present invention relates to a compound named Mumbaistatin which is obtainable by cultivation of the microorganism HIL-008003 (DSM 11641), and to its pharmaceutically acceptable salts and derivatives. Mumbaistatin is a glucose-6-phosphate translocase inhibitor and can be used in the treatment of diabetes mellitus. The present invention further relates to a process for the production of Mumbaistatin, to the microorganism HIL-008003 (DSM 11641), to the use of Mumbaistatin and its pharmaceutically acceptable salts and derivatives as pharmaceuticals, in particular for their use in the treatment of diabetes mellitus, and to pharmaceutical compositions comprising Mumbaistatin or a pharmaceutically acceptable salt or derivative thereof.

Increased rate of hepatic glucose output is a general feature of diabetes mellitus. In particular, there is a strong correlation between fasting plasma glucose level in non-insulin dependent diabetes mellitus (NIDDM) and hepatic glucose output. The two pathways by which glucose is produced in the liver are gluconeogenesis and glycogenolysis. The terminal steps of both pathways are catalyzed by the microsomal glucose-6-phosphatase, a key enzyme in the homeostatic regulation of blood glucose levels. The level of this enzyme has also been known to be elevated in both experimental and pathological conditions of diabetes. Interference with this enzyme system should, therefore, result in a reduced hepatic glucose production.

Hepatic glucose-6-phosphatase is a multicomponent system comprised of at least three functional activities: a glucose-6-phosphate translocase (T1), a glucose-6-phosphate phosphohydrolase and a phosphate/pyrophosphate translocase (T2). The glucose-6-phosphate translocase facilitates transport of glucose-6-phosphate into the lumen of the endoplasmic reticulum (ER). The phosphohydrolase, with its active site situated on the lumenal surface of the ER, hydrolyses glucose-6-phosphate and releases glucose and phosphate into the lumen. While the efflux of phosphate is facilitated by the phosphate/pyrophosphate translocase, the exact mechanism of glucose efflux is still not clear.

The high degree of substrate specificity of glucose-6-phosphate translocase makes this a potential target for pharmacological intervention in the treatment of diabetes mellitus. Thus, amongst physiologically occurring sugar phosphates, only glucose-6-phosphate is transported by the translocase. In contrast, the phosphatase is non-specific and is known to hydrolyze a variety of organic phosphate esters. A series of non-specific inhibitors of glucose-6-phosphatase has been described in the literature, e.g. phlorrhizin (J. Biol. Chem. 242, 1955–1960 (1967)), 5,5'-dithiobis-2-nitrobenzoic acid (Biochem. Biophys. Res. Commun. 48, 694–699 (1972)), 2,2'-diisothiocyanatostilbene and 2-isothiocyanato-2'-acetoxystilbene (J. Biol. Chem. 255, 1113–1119 (1980)). The first therapeutically utilizable inhibitors of the glucose-6-phosphatase system are proposed in European patent applications EP-A-587 087 and EP-A-587 088. Kodaistatins A, B, C, and D described in international patent application no. PCT/EP 98/02247 are the first glucose-6-phosphate translocase inhibitors from microbial sources.

DETAILED DESCRIPTION OF THE DRAWINGS

Figure 1:
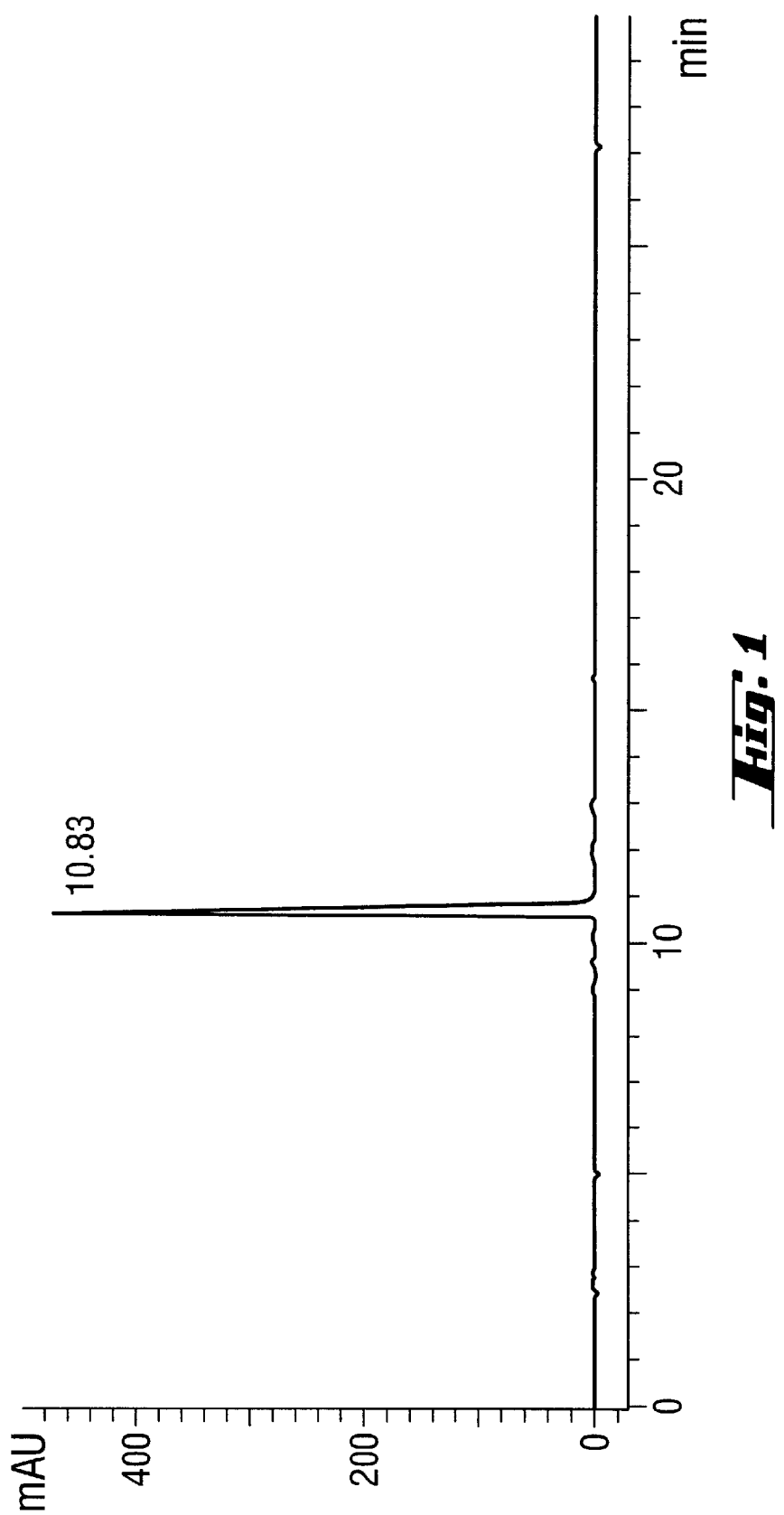
FIG. 1 shows the HPLC trace of Mumbaistatin.

It has now been found that from a different microbial source a novel compound with high glucose-6-phosphate translocase inhibitory activity is obtainable which has been named Mumbaistatin. The present invention thus relates to a compound named Mumbaistatin, which has the molecular formula $C_{28}H_{20}O_{12}$ and which is characterized by any one or more of its physico-chemical and spectral properties given below, such as its $^1H$ NMR spectroscopic data depicted in the $^1H$ NMR spectrum in FIG. 9 and its $^{13}C$ NMR spectroscopic data depicted in the $^{13}C$ NMR spectrum in FIG. 10, and to the pharmaceutically acceptable salts and derivatives thereof, such as esters, ethers and obvious chemical equivalents, including all stereoisomeric forms and all tautomeric forms.

Mumbaistatin has a hitherto unreported novel structure belonging to quinone class of compounds. A chemical abstract literature search using search keys of the molecular formula established Mumbaistatin to be a novel compound. No other compound represented the structural features of Mumbaistatin.

Mumbaistatin is obtainable by cultivation of a microorganism referred to as culture no. HIL-008003 or also as culture no. Y-9645974 (henceforth referred to as HIL-008003). This microorganism used for the production of Mumbaistatin was isolated from a soil sample collected from the Hiranyakeshi riverbed near Amboli, Maharashtra, India. The microorganism HIL-008003 has been identified as *Streptomyces litmocidini*. The microorganism was deposited on Jul. 4, 1997, with the German Collection of Microorganisms and Cell Cultures (DSMZ-Deutsche Sammlung von Mikroorganismen und Zellkulturen GmbH), Mascheroder Weg 1b, D-38124, Braunschweig, Germany and given the accession number DSM 11641.

Thus, the present invention further provides a process for the production of the novel compound named Mumbaistatin and its pharmaceutically acceptable salts and derivatives from Streptomyces species HIL-008003, its mutants and variants. The said process comprises cultivation of culture no. HIL-008003, its mutants or variants, under aerobic conditions in a nutrient medium containing one or more sources of carbon and one or more sources of nitrogen and optionally nutrient inorganic salts and/or trace elements, followed by isolation of the said compound and purification in a customary manner.

The nutrient medium preferably contains sources of carbon, nitrogen and nutrient inorganic salts and optionally trace elements. The carbon sources are, for example, starch, glucose, sucrose, dextrin, fructose, molasses, glycerol, lactose or galactose, preferably glucose. The sources of nitrogen are, for example, soybean meal, peanut meal, yeast extract, beef extract, peptone, tryptone, malt extract, corn steep liquor, gelatin or casamino acids, preferably soybean meal and corn steep liquor. The nutrient inorganic salts and trace elements are, for example, sodium hydrogen phosphate, potassium hydrogen phosphate, sodium chloride, cobalt chloride, calcium chloride, calcium carbonate, potassium nitrate, ammonium sulfate or magnesium sulfate, preferably cobalt chloride and calcium carbonate.

Cultivation of culture no. HIL-008003 is usually carried out at temperatures between 25–30° C. and pH between 6.0 and 8.0. Preferably culture no. HIL-008003 is cultivated at 27° C. (±1° C.) and pH 7.0.

The fermentation of HIL-008003 is preferably carried out for about 40 to 70 hours in order to obtain an optimal yield of Mumbaistatin. It is particularly preferred to carry out the fermentation for about 40 to 48 hours under submerged conditions, for example, in shake flasks as well as in laboratory fermenters. If desired, DESMOPHEN® (polypropylene oxide) may be used as an antifoam agent in the fermenters. The progress of fermentation and formation of Mumbaistatin can be detected by measuring the inhibition of glucose-6-phospate translocase activity in untreated and TRITON X-100® disrupted rat liver microsomes in microtiter plates at room temperature using a calorimetric assay as described in *Methods in Enzymology* 174, 58–67 (1989) with some modifications. In the resulting culture broth, Mumbaistatin is present primarily in the culture filtrate and can thus be recovered by extraction of the culture filtrate with a water immiscible solvent such as, for example, ethyl acetate, dichloromethane, chloroform or butanol at pH 5–8, or by hydrophobic interaction chromatography using polymeric resins such as DIAION® HP-20 (Mitsubishi Chemical Industries Limited, Japan), AMBERLITE® XAD (Rohm and Haas Industries, U.S.A.), or activated charcoal, or by ion exchange chromatography at pH 5–8. The preferred method is adsorption over DIAION® HP-20 followed by desorption of the compound using eluants such as water, methanol, acetone, acetonitrile, n-propanol, isopropanol or combinations thereof. Concentration and lyophilization of the active eluates gives the crude compound.

The crude material can be further purified by using any of the following techniques: by normal phase chromatography using alumina or silica gel as stationary phase and eluants such as ethyl acetate, chloroform, methanol or combinations thereof; by reverse phase chromatography using reverse phase silica gel like dimethyloctadecylsilylsilica gel, also called RP-18, or dimethyloctylsilylsilica gel, also called RP-8, as stationary phase and eluants such as water, buffers such as phosphate, acetate, citrate (pH 2–8), and organic solvents such as methanol, acetonitrile, acetone, tetrahydrofuran or combinations of these solvents; by gel permeation chromatography using resins such as SEPHADEX® LH-20 (Pharmacia Chemical Industries, Sweden), TSKgel TOYOPEARL® HW-40F (TosoHaas, Tosoh Corporation, Japan) in solvents such as methanol, chloroform, acetone, ethyl acetate or combinations of these solvents or SEPHADEX® G-0 and G-25 in water; or by counter-current chromatography using a biphasic eluant system made up of two or more solvents such as water, methanol, ethanol, isopropanol, n-propanol, tetrahydrofuran, acetone, acetonitrile, methylene chloride, chloroform, ethyl acetate, petroleum ether, benzene and toluene. These techniques may be used repeatedly, or a combination of the different techniques may be used. The preferred method is chromatography over TOYOPEARL® followed by reverse phase modified silica gel (RP-18).

The compound Mumbaistatin may be converted into pharmaceutically acceptable salts and derivatives, like esters and ethers and other obvious chemical equivalents, which are all covered by the present invention. The invention also covers all salts and derivatives of Mumbaistatin which themselves are not suitable for use as pharmaceuticals but which can be used as intermediates in the preparation of pharmaceutically acceptable salts and derivatives. The invention covers Mumbaistatin and all its salts and derivatives in all their stereoisomeric forms and tautomeric forms. The salts and derivatives can be prepared by standard procedures known to one skilled in the art. Salts like sodium and potassium salts, for example, may be prepared by treating Mumbaistatin with suitable sodium or potassium bases.

Esters may be prepared, for example, by reacting Mumbaistatin with carboxylic acids in the presence of reagents such as dicyclohexylcarbodiimide (DCC), or by treating the compound with acylating agents such as acid chlorides. Other methods of preparation of esters are given in the literature, for example in J. March, *Advanced Organic Synthesis*, 4th Edition, John Wiley & Sons, 1992.

The esters of Mumbaistatin covered by the present invention include intramolecular esters, i.e. lactones. A compound specifically mentioned as being a subject of the present invention is the compound which has been named L970860 and the pharmaceutically acceptable salts and derivatives thereof, in all their stereoisomeric and tautomeric forms. Compound L970860 is a lactone obtainable by treatment of Mumbaistatin with trifluoroacetic acid. It has the molecular formula $C_{28}H_{18}O_{11}$ is characterized by any one or more of its physico-chemical and spectral properties given below, such as its $^1$H NMR spectroscopic data depicted in the $^1$H NMR spectrum in FIG. 7 and its $^{13}$C NMR spectroscopic data depicted in the $^{13}$C NMR spectrum in FIG. 8. Lactonization of Mumbaistatin to give L970860 may be used for the purpose of isolating or purifying Mumbaistatin.

Ethers may be prepared, for example, from Mumbaistatin by reaction with alkylating agents under basic conditions. Other methods of preparation of ethers are given in the literature, for example in *Advanced Organic Synthesis*, 4th Edition, J. March, John Wiley & Sons, 1992.

Mumbaistatin potently inhibits rat liver microsomal glucose-6-phosphate translocase. The results obtained in pharmacological tests are given below. Mumbaistatin and its pharmaceutically acceptable salts and derivatives are therefore useful as pharmaceutically active ingredients, in particular in the treatment of diabetes mellitus, and more generally in the treatment or prophylaxis of conditions which are caused by or associated with an elevated activity of glucose-6-phosphate translocase, or of conditions in which it is intended to reduce glucose-6-phosphate translocase activity. Mumbaistatin and its pharmaceutically acceptable salts and derivatives can be administered to animals, preferably to mammals, and in particular to humans as pharmaceuticals on their own, in mixtures with one another and in the form of pharmaceutical compositions which permit enteral or parenteral administration. Accordingly, the present invention also relates to Mumbaistatin and its pharmaceutically acceptable salts and derivatives for use as pharmaceuticals and to the use of Mumbaistatin and its pharmaceutically acceptable salts and derivatives for the production of medicaments for reducing glucose-6-phosphate translocase activity, in particular for the production of medicaments for the treatment of diabetes mellitus. The present invention further relates to pharmaceutical compositions that contain an effective amount of Mumbaistatin and/or one or more pharmaceutically acceptable salts and/or derivatives thereof together with a pharmaceutically acceptable carrier.

Mumbaistatin can be administered orally, intramuscularly, intravenously or by other modes of administration. Pharmaceutical compositions, which contain Mumbaistatin or a pharmaceutically acceptable salt or derivative thereof singly or in combinations, can be prepared according to standard techniques by mixing the compound (s) with one or more pharmacologically acceptable excipients and/or auxiliaries such as, for example, fillers, emulsifiers, lubricants, masking flavors, colorants or buffer substances, and converting the mixture into a suitable pharmaceutical form such as, for example, tablets, coated tablets, capsules or a suspension or solution suitable for enteral or parenteral administration.

Examples of auxiliaries and/or excipients that may be utilized are starch, tragacanth, lactose, talc, agar-agar, polyglycols, ethanol and water. Suspensions or solutions in water are suitable and preferred for parenteral administration. It is also possible to administer the active substances as such, without vehicles or diluents, in a suitable form, for example, in capsules. Pharmaceutical compositions comprising Mumbaistatin or a pharmaceutically acceptable salt or derivative thereof may also contain other pharmaceutically active ingredients.

As customary, the galenic formulation and the method of administration as well as the dosage range which are suitable in a specific case depend on the species to be treated and on the state of the respective condition or disease, and can be optimized using methods known in the art.

Apart from use as pharmaceutically active ingredients and as intermediates in the production of derivatives, Mumbaistatin and its salts and derivatives can also be employed as auxiliaries for diagnostic purposes, for example in in vitro diagnoses, and for research purposes in biochemical investigations in which an inhibition of glucose-6-phosphate translocase is desired.

The following examples are illustrative of the present invention, but do not limit the scope thereof.

Abbreviations: MeOH Methanol; DMSO Dimethylsulfoxide; TFA Trifluoroacetic Acid

EXAMPLE 1
Isolation of the Culture HIL-008003 From Soil
(a) Composition of nutrient isolation medium

| | |
|---|---|
| Corn starch | 10.0 g |
| Casein | 1.0 g |
| Peptone | 1.0 g |
| Yeast extract | 1.0 g |
| K$_2$HPO$_4$ | 0.5 g |
| Agar powder | 13.0 g |
| Demineralized water | 1.0 liter |
| pH | 7.5 |

(b) Soil plating and isolation 10 g of soil collected from the Hiranyakeshi riverbed near Amboli, Maharashtra, India was added to 90 ml of sterilized demineralized water in a 250 ml Erlenmeyer flask that was then shaken for 2 hours on a rotary shaker (220 rpm). The above soil suspension was then serially diluted in steps of 10 up to $10^{-5}$. From the last dilution, 1 ml of suspension was placed at the center of a sterile glass petri plate (15 cm diameter) in which was then poured approximately 50 ml of the above isolation medium supplemented with 25 µg/ml of amphotericin B as an antifungal agent. The medium was cooled to 45° C. before pouring and the plate swirled thoroughly. The mixture of soil suspension and medium was allowed to settle and incubated at 28° C. (±1° C.) for 7 days.

The petri plate was periodically observed and the microorganism culture no. HIL-008003 (culture no. Y-9645974) was isolated from amongst the growing microorganisms.

EXAMPLE 2
Maintenance of the Culture HIL-008003

Culture no. HIL-008003 was maintained on the following medium:

| | |
|---|---|
| Malt extract | 10.0 g |
| Yeast extract | 4.0 g |
| Glucose | 4.0 g |
| Agar powder | 13.0 g |
| Demineralized water | 1.0 liter |
| pH | 7.0 |

After dissolving the above-mentioned ingredients thoroughly by heating, it was distributed in test tubes and then sterilized at 121° C. for 20 minutes. The test tubes were then cooled and allowed to solidify in a slanting position. The agar slants were streaked with the growth of the culture no. HIL-008003 by a wire loop and incubated at 28° C. (±1° C.) until a good growth was observed. The well-grown cultures were stored in the refrigerator at 8° C.

EXAMPLE 3
Fermentation of Culture HIL-008003 in Shake Flasks

Composition of seed medium:

| | |
|---|---|
| Glucose | 15.0 g |
| Soybean meal | 15.0 g |
| Corn steep liquor | 5.0 g |
| NaCl | 5.0 g |
| CaCO$_3$ | 2.0 g |
| Demineralized water | 1.0 liter |
| pH | 7.0 |

The above seed medium was distributed in 80 ml amounts in 500 ml Erlenmeyer flasks and autoclaved at 121° C. for 20 minutes. The flasks were cooled to room temperature and each flask was then inoculated with a loopful of the above mentioned well grown culture of Example 2 and shaken on a rotary shaker for 72 hours at 240 rpm at 27° C. (±1° C.) to give seed culture.

Composition of the production medium

| | |
|---|---|
| Glucose | 20.0 g |
| Soybean meal | 10.0 g |
| CaCO$_3$ | 0.2 g |
| Cobalt chloride | 0.001 g |
| Demineralized water | 1.0 liter |
| pH | 7.0 |

The production medium was distributed in 60 ml amounts in 500 ml Erlenmeyer flasks and autoclaved at 121° C. for 20 minutes. The flasks were cooled to room temperature and then inoculated with the above mentioned seed culture (1% v/v). The fermentation was carried out on a rotary shaker at 240 rpm and at a temperature of 27° C. (±1° C.) for 40–48 hours.

The production of Mumbaistatin was monitored by measuring the inhibition of glucose-6-phosphate translocase. After harvesting, the culture broth was centrifuged and Mumbaistatin was isolated from the culture filtrate and purified as described in Example 5.

EXAMPLE 4
Fermentation of Culture HIL-008003 in Fermenters

Stage 1: Preparation of Seed Culture in Shake Flasks

The seed medium of Example 3 was distributed in 160 ml amounts in 1 L Erlenmeyer flasks and autoclaved for 20 minutes. The seed culture was grown in these flasks as described in Example 3.

Stage 2: Preparation of Seed Culture in Fermenter 80 liters of the seed medium, as described in Example 3, in a 100 liter Marubishi fermenter was sterilized in situ for 45 minutes at 121° C., cooled to 27° C.±1° C. and seeded with 4.5 liters of the seed culture mentioned above.

The fermentation was run with the following parameters:

| | |
|---|---|
| Temperature | 27° C. (±0.5° C.) |
| Agitation | 80 rpm |
| Aeration | 50 lpm |
| Harvest time | 24 hours |

Stage 3: Large Scale Fermentation 700 liters of the production medium, as described in Example 3, in a 1000 liter Marubishi fermenter along with 150 ml of DESMOPHEN® (polypropylene oxide) as antifoam agent was sterilized in situ for 45 minutes at 121° C., cooled to 27° C.±1° C. and seeded with 75 liter seed culture from Stage 2.

The fermentation was run with the following parameters:

| | |
|---|---|
| Temperature | 27° C. (±0.5° C.) |
| Agitation | 50 rpm |
| Aeration | 450 lpm |
| Harvest time | 40–44 hours |

The production of the compound was monitored by measuring the inhibition of glucose-6-phosphate translocase. When fermentation was discontinued, the pH of the culture broth was 6.0–7.0. The culture broth was centrifuged after harvesting and the glucose-6-phosphate translocase inhibitor Mumbaistatin was isolated from the culture filtrate as described below in Example 5.

EXAMPLE 5
Isolation and Purification of Mumbaistatin

Approximately 1000 liters of culture broth were harvested and separated from mycelium (12 kg) by centrifugation. The desired compound Mumbaistatin was found to be present primarily in the culture filtrate. The culture filtrate (730 liters) was passed through a column of DIAION® HP-20 (28 liters, 3–4% v/v). The column was thoroughly washed with demineralized water (250 liters) and then eluted with a step gradient of MeOH in water. Thus, the elution was done with 10% MeOH (120 liters) and 40% MeOH (300 liters). The fractions were collected in 15 liters size. The active eluates (15×16 liters) obtained with 40% MeOH, were combined, concentrated under reduced pressure of 10–100 mm of Hg at 35° C. and lyophilized to yield 240 g of active crude material showing an $IC_{50}$ of 5 $\mu$g/ml.

The crude material (240 g) was passed through a second HP-20 column. The column was thoroughly washed with demineralized water (150 liters) and then eluted with a step gradient of MeOH in water. Thus, the elution was done with 20% MeOH (80 liters) and 40% MeOH (100 liters). The fractions were collected in 10 liters and 2 liter sizes respectively. The active eluates (2×30 liters) obtained with 40% MeOH, were combined, concentrated under reduced pressure of 10–100 mm of Hg at 35° C. and lyophilized to yield 20 g of enriched material showing an $IC_{50}$ of 1 $\mu$g/ml.

The enriched material, thus obtained, was purified by two successive gel permeation chromatographies on SEPHADEX® LH-20 with varying substrate to gel ratios. The above enriched material was passed separately in 4 lots of 5 g each through SEPHADEX® LH-20 (1.5 liters) packed in 4 cm×120 cm glass column. The mobile phase was water and the flow rate was maintained at 2.5 ml/min. The fractions were collected in 25 ml aliquots. The active eluates were monitored by HPLC on a LICHROCART® 100 RP-18 (250 mm×4 mm) column using a gradient of 0.1% aqueous TFA to $CH_3CN$ in 20 min at a flow rate of 1 ml/min and detection at 270 nm. The active eluates with the desired component were pooled and concentrated under reduced pressure of 10–100 mm of Hg at 35° C. and lyophilized to obtain 1 g of highly enriched material with an $IC_{50}$ of 0.1–0.3 $\mu$g/ml.

The above material was further purified in 2 lots of 500 mg each by passing through SEPHADEX® LH-20 packed in a glass column (2.5 cm×110 cm). The mobile phase was water and the flow rate was maintained at 0.5 ml/min. The fractions were collected in 6 ml aliquots. Fractions were pooled based on HPLC (conditions mentioned above). The active fractions with the desired compound were pooled, concentrated under reduced pressure of 10–100 mm of Hg at 35° C. and lyophilized to obtain 160 mg of semi-pure compound having an $IC_{50}$ of 0.06 $\mu$g/ml.

Finally, the semi-pure material was purified by preparative HPLC on a EUROSPHERE® 100 C18, 10 $\mu$(250×16 mm) column using a gradient of 5% methanol in water to 40% methanol in water in 30 min. The flow rate was maintained at 6 ml/min and the detection was at 270 nm to obtain pure Mumbaistatin (70 mg).

Mumbaistatin gave poor quality $^1H$ NMR and $^{13}C$ NMR spectra. The characterization of the parent compound Mumbaistatin was therefore primarily based on the spectral analysis of the lactone L970860 which was obtained by treatment of Mumbaistatin with TFA using the method described in Example 6.

EXAMPLE 6
Preparation of the Lactone L970860

0.1% TFA (50 ml) was added to 70 mg of Mumbaistatin dissolved in methanol (5 ml), and the reaction mixture was heated for 1 hour at 50° C. The mixture was then evaporated under reduced pressure of 10–100 mm of Hg at 35° C. to dryness. The reaction product, thus obtained, was purified by preparative HPLC on a EUROSPHERE® 100, C18, 10 $\mu$(250 mm×16 mm) column using a gradient of 30% $CH_3CN$ in 0.1% TFA to 80% $CH_3CN$ in 0.1% TFA in 20 min at a flow rate of 6 ml/min and detection at 270 nm to give pure L970860 (55 mg).

The physico-chemical and spectral properties of Mumbaistatin and the lactone L970860 are summarized in Table 1. The spectroscopic data of the compounds are given in FIGS. 2, 3 and 5 to 10 of the drawings. FIGS. 1 and 4 show HPLC chromatograms. The content of the individual drawings is indicated in Table 1.

TABLE 1

| | Mumbaistatin | L970860 |
|---|---|---|
| Nature | Reddish brown solid | Reddish brown solid |
| Solubility | MeOH and DMSO | MeOH and DMSO |
| Melting point | >250° C. (decomp.) | >250° C. (decomp.) |

TABLE 1-continued

Figure 2:
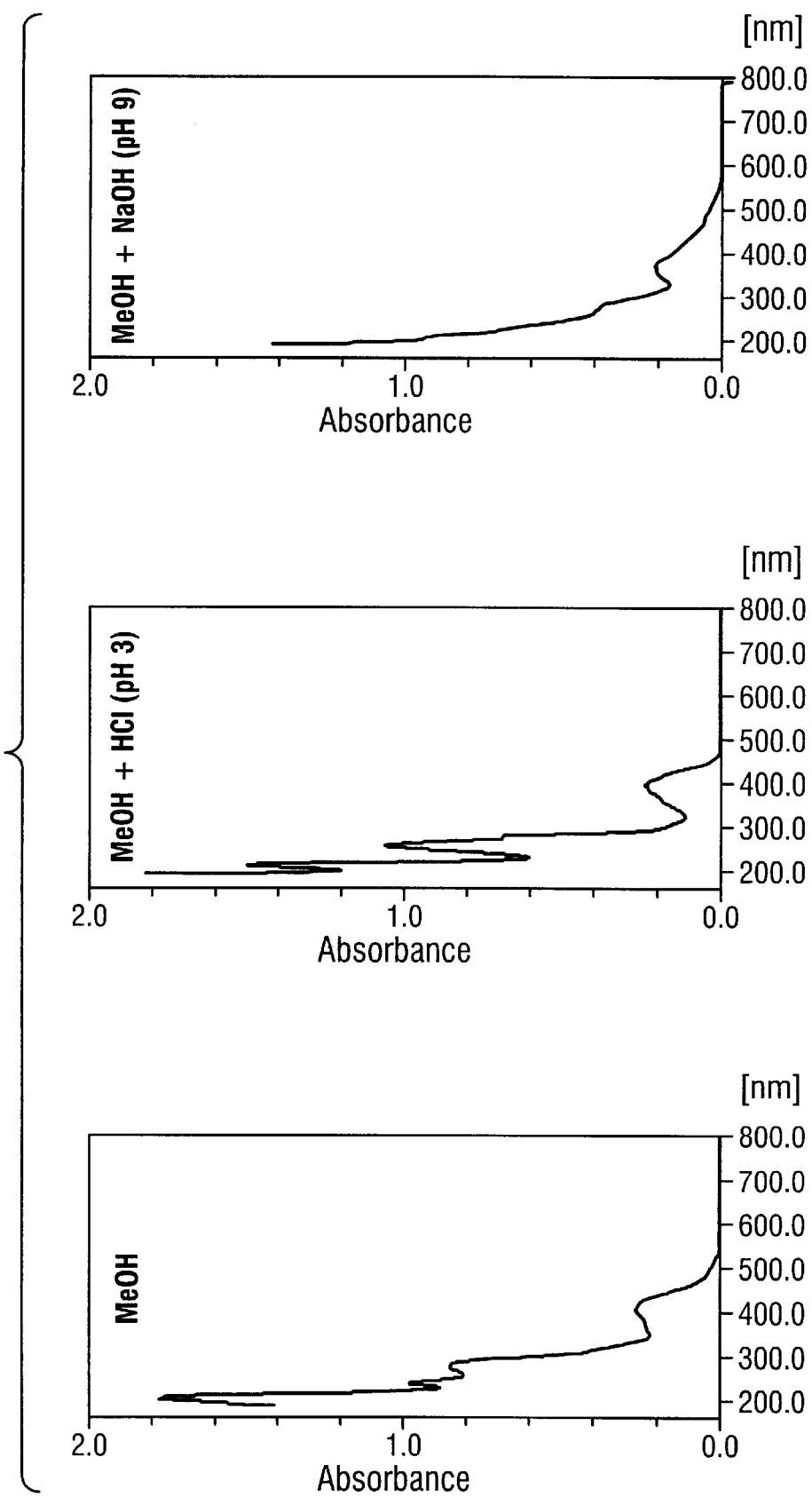
FIG. 2 illustrates the UV spectrum of Mumbaistatin.
Figure 3:
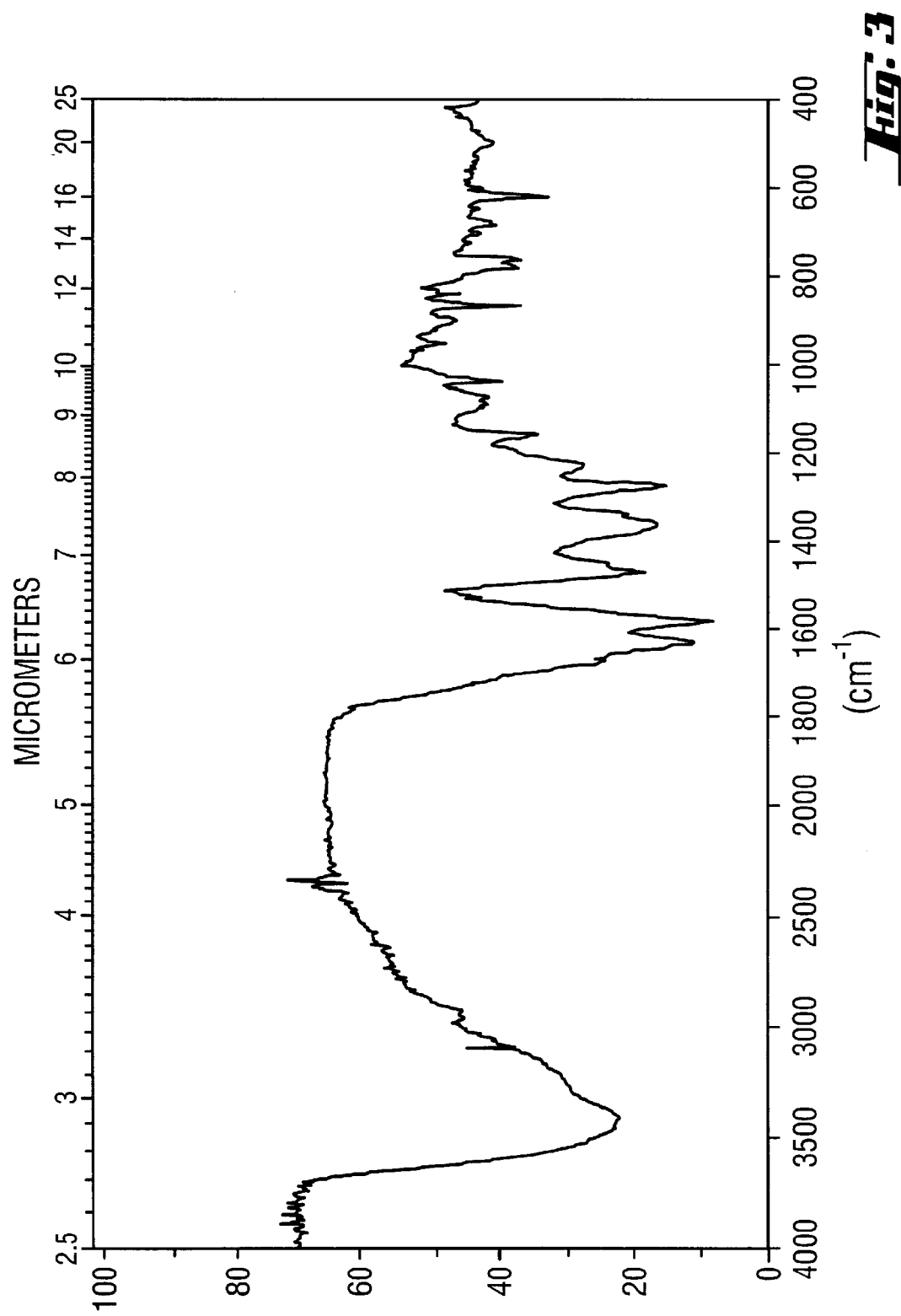
FIG. 3 depicts the IR spectrum of Mumbaistatin in KBr.
Figure 4:
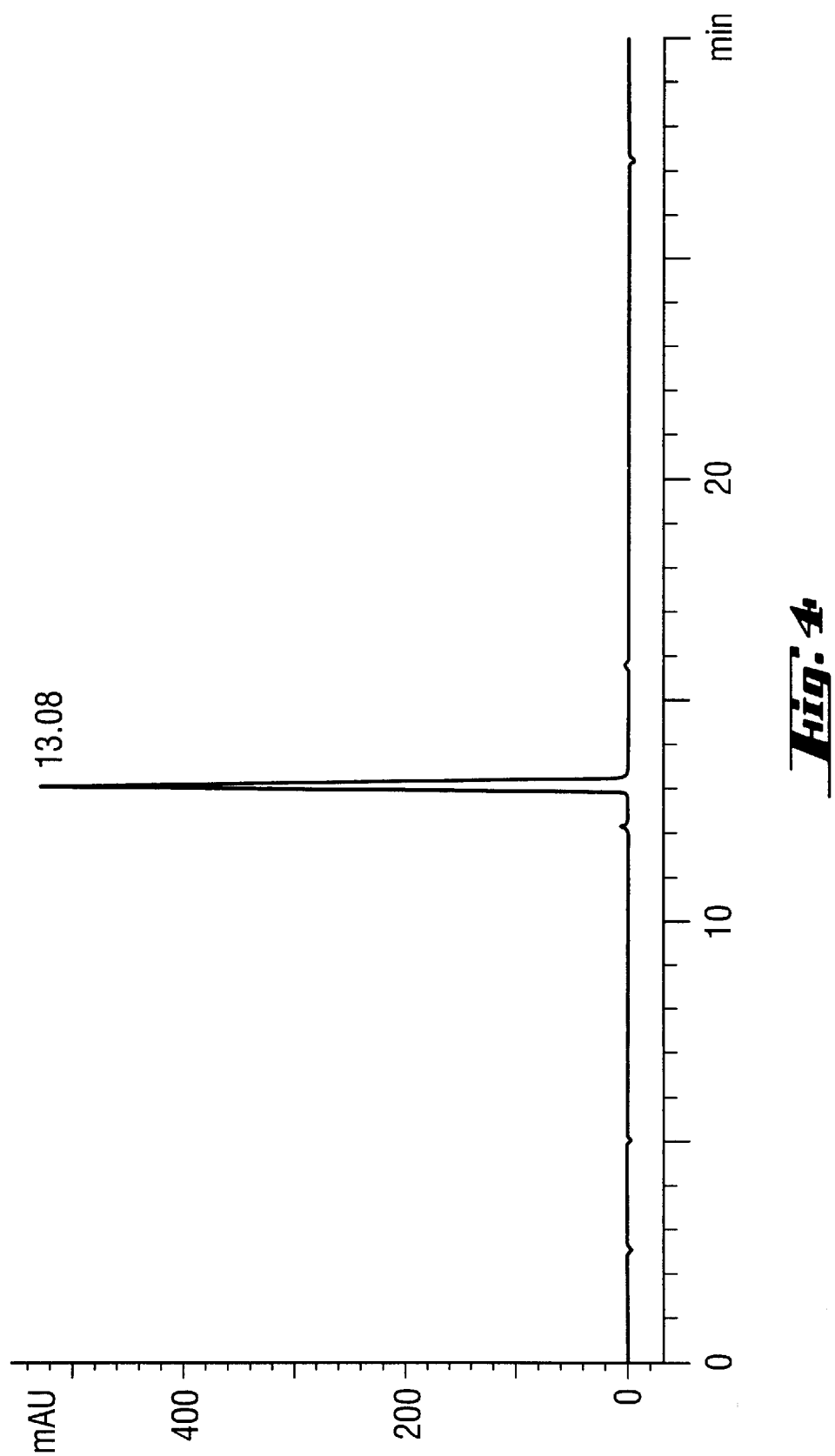
FIG. 4 shows the HPLC trace of L970860.
Figure 5:
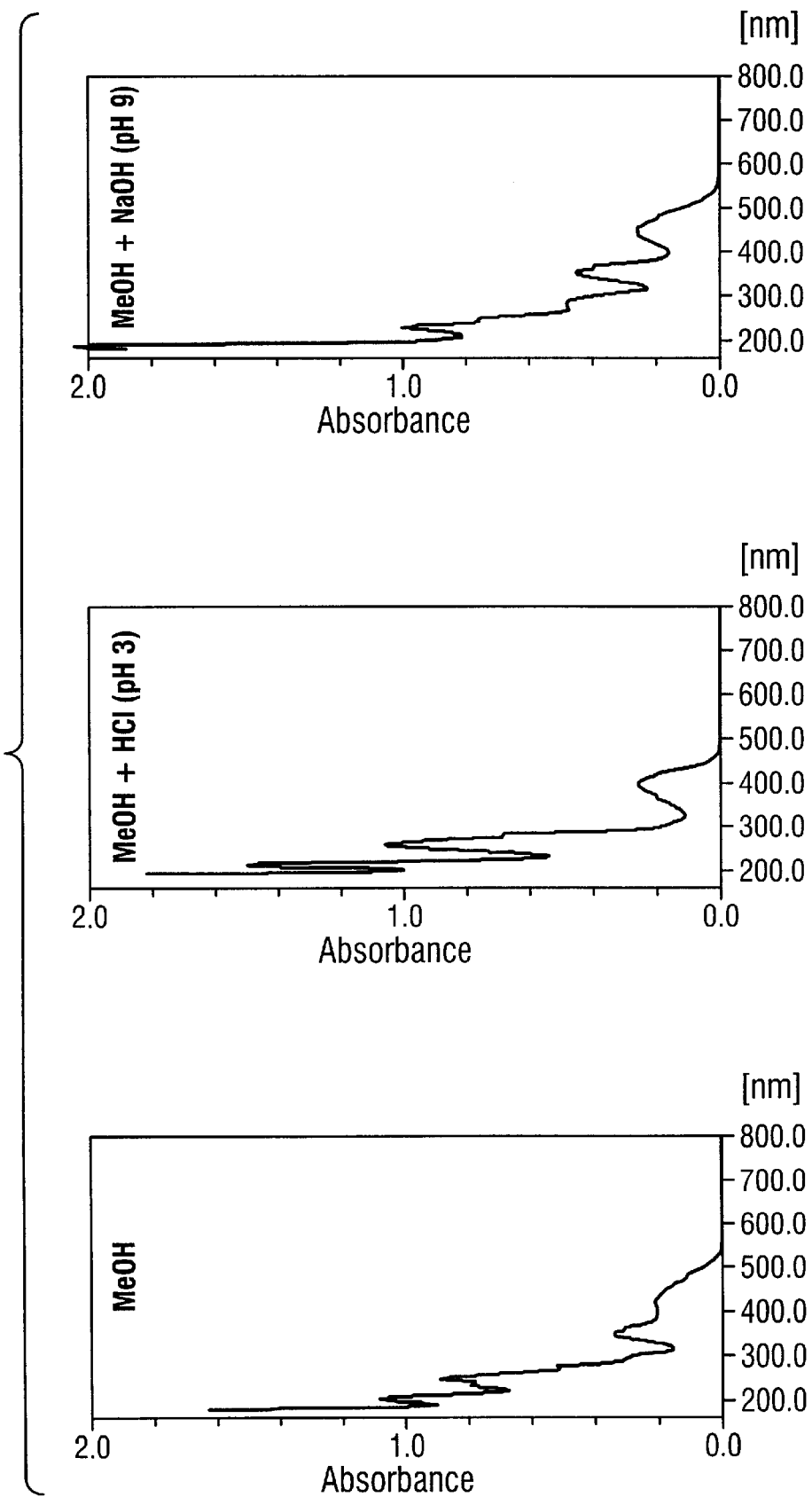
FIG. 5 illustrates the UV spectrum of L970860.
Figure 6:
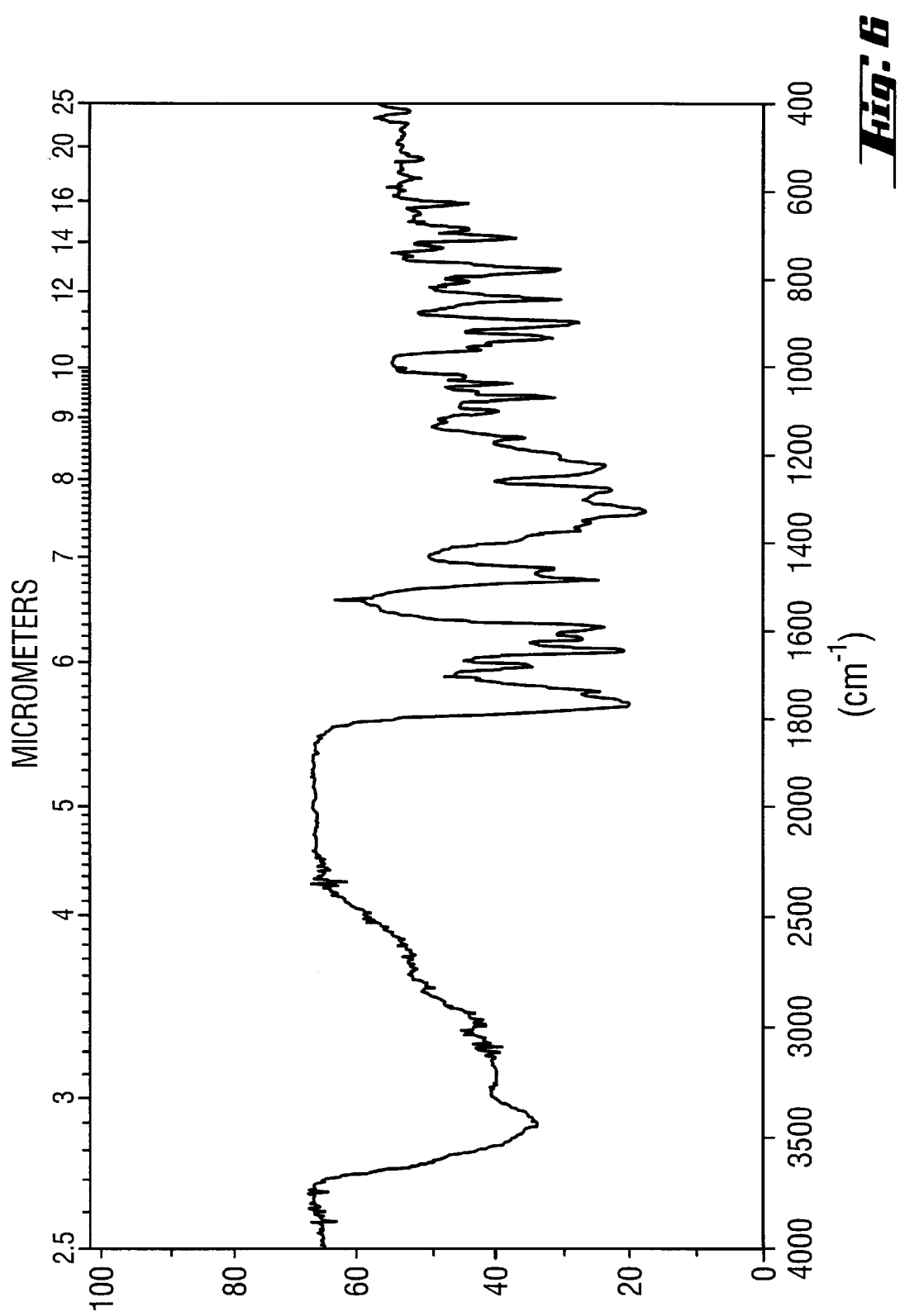
FIG. 6 depicts the IR spectrum of L970860 in KBr.
Figure 7:
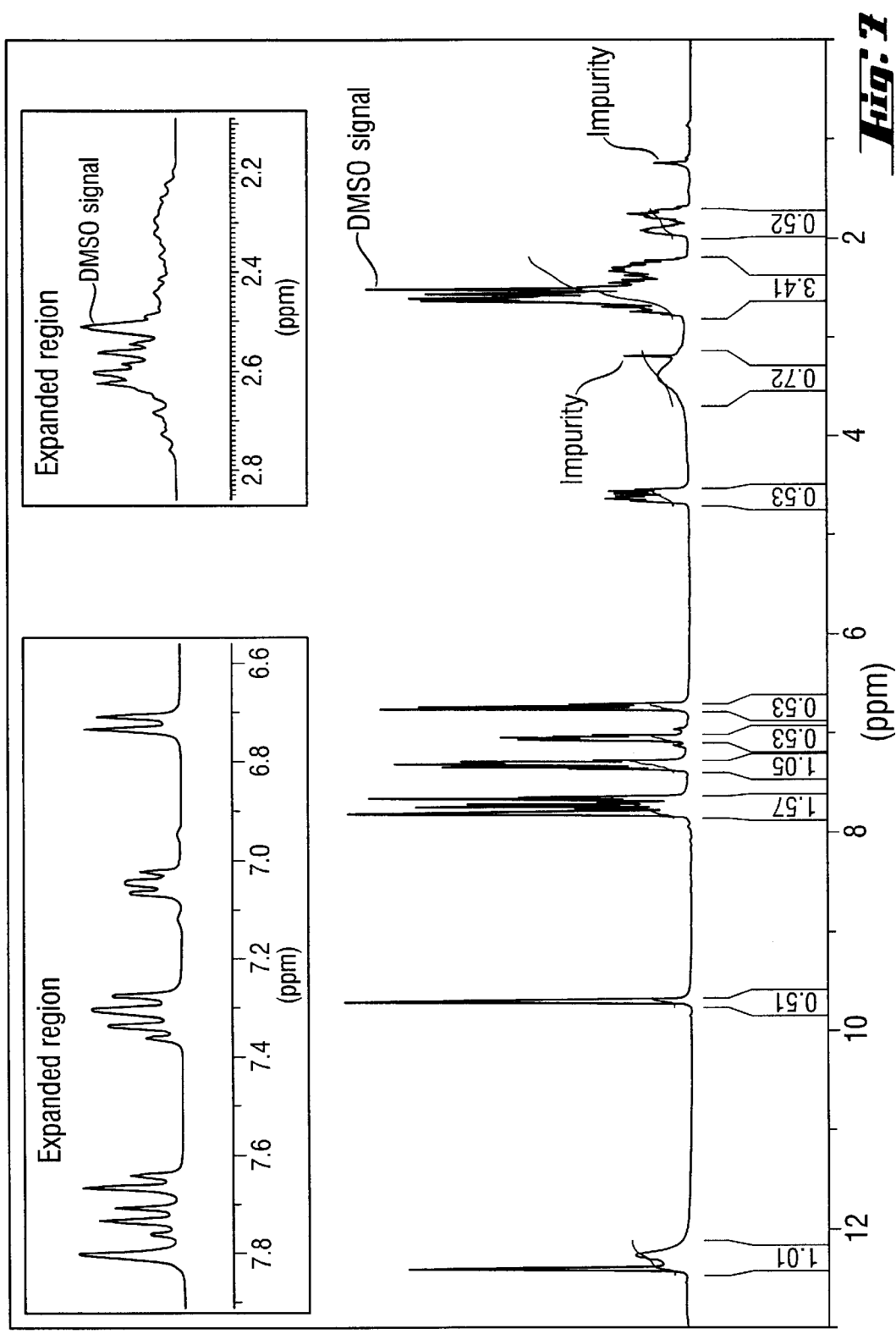
FIG. 7 shows the proton NMR spectrum of L970860 at 300 MHz in $d_6$-DMSO.
Figure 8:
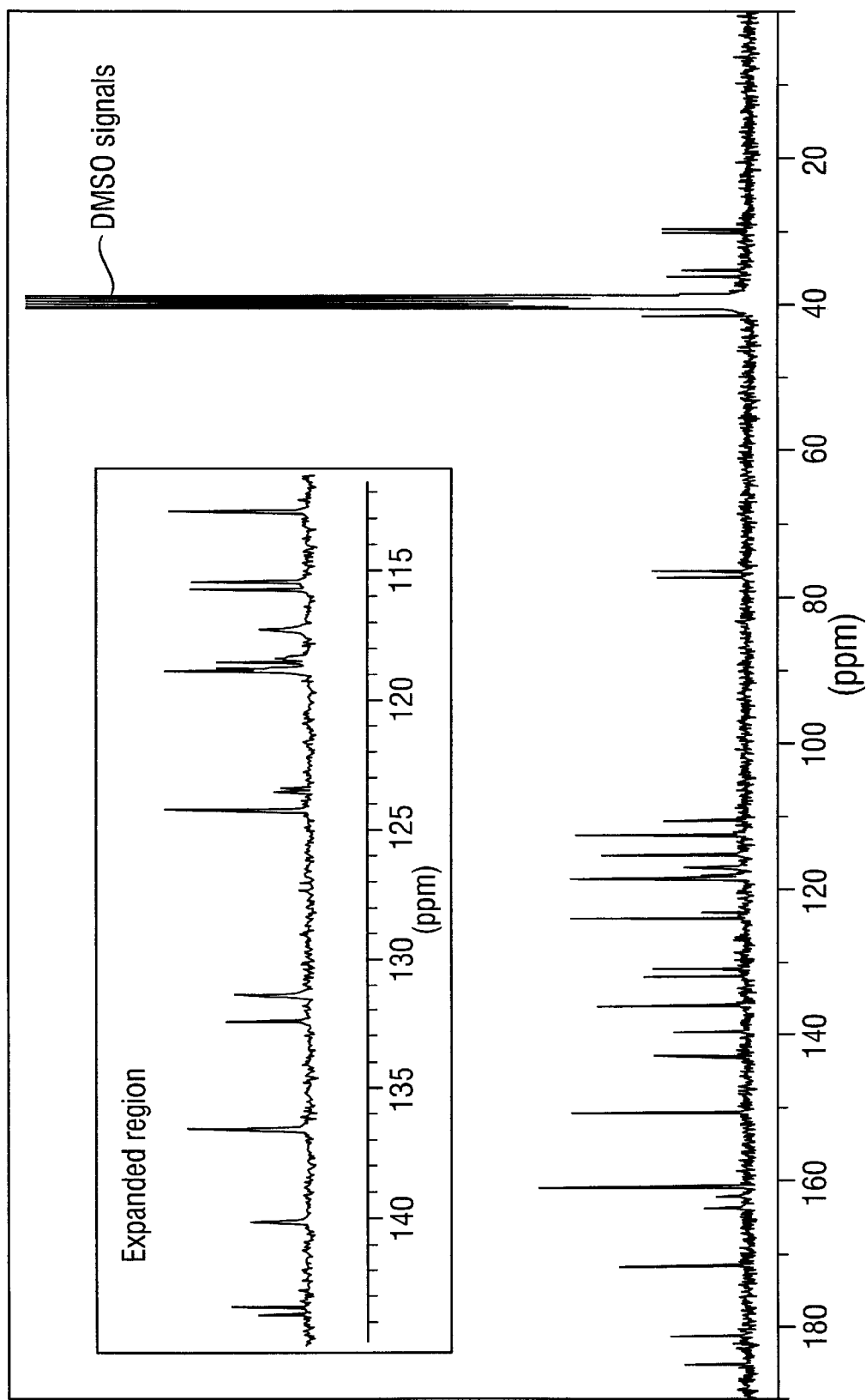
FIG. 8 shows the $^{13}C$ NMR spectrum of L970860 at 75 MHz in $d_6$-DMSO.
Figure 9:
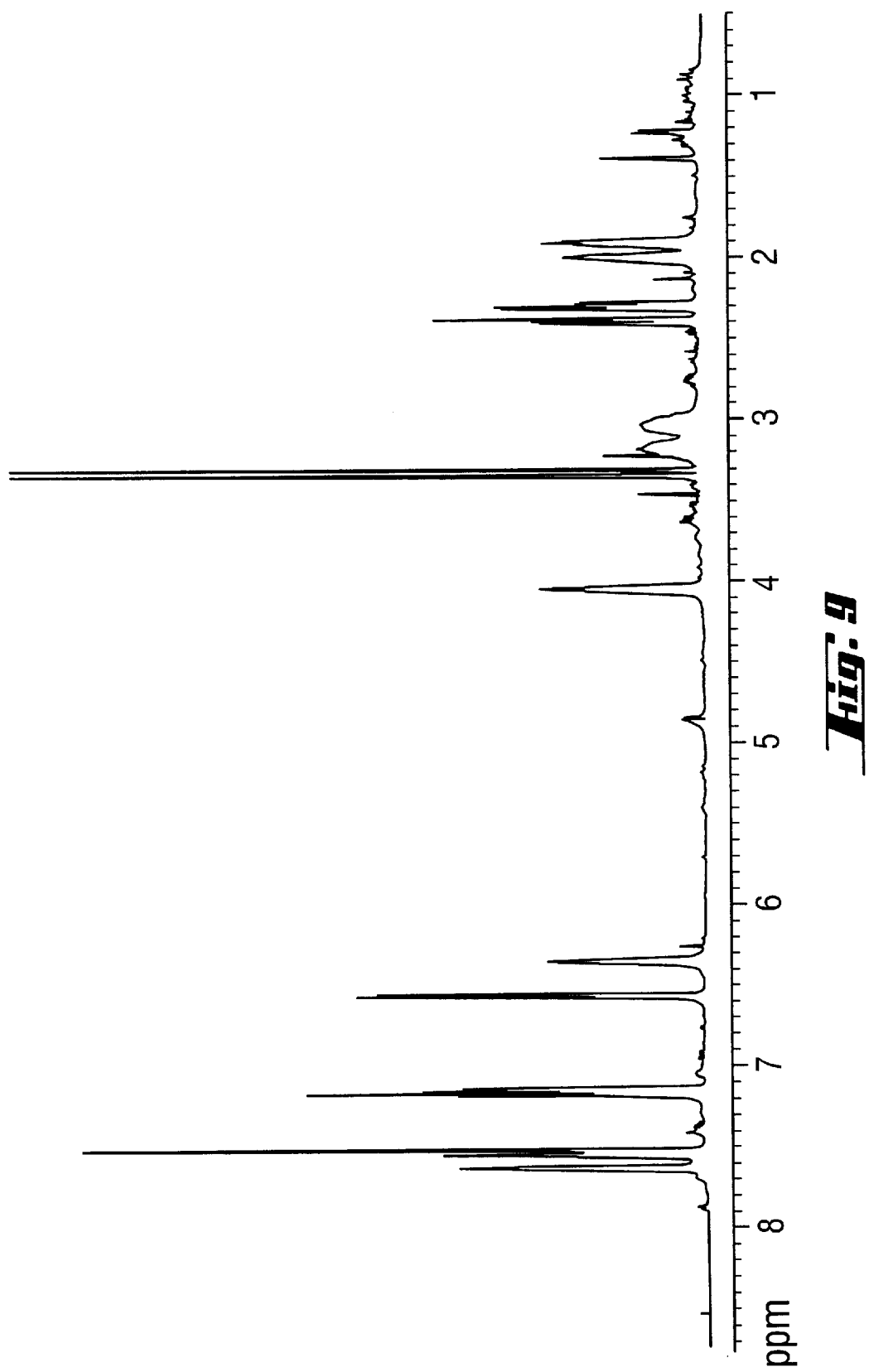
FIG. 9 shows the proton NMR spectrum of Mumbaistatin at 600 MHz in $d_4$-MeOH at 27° C.
Figure 10:
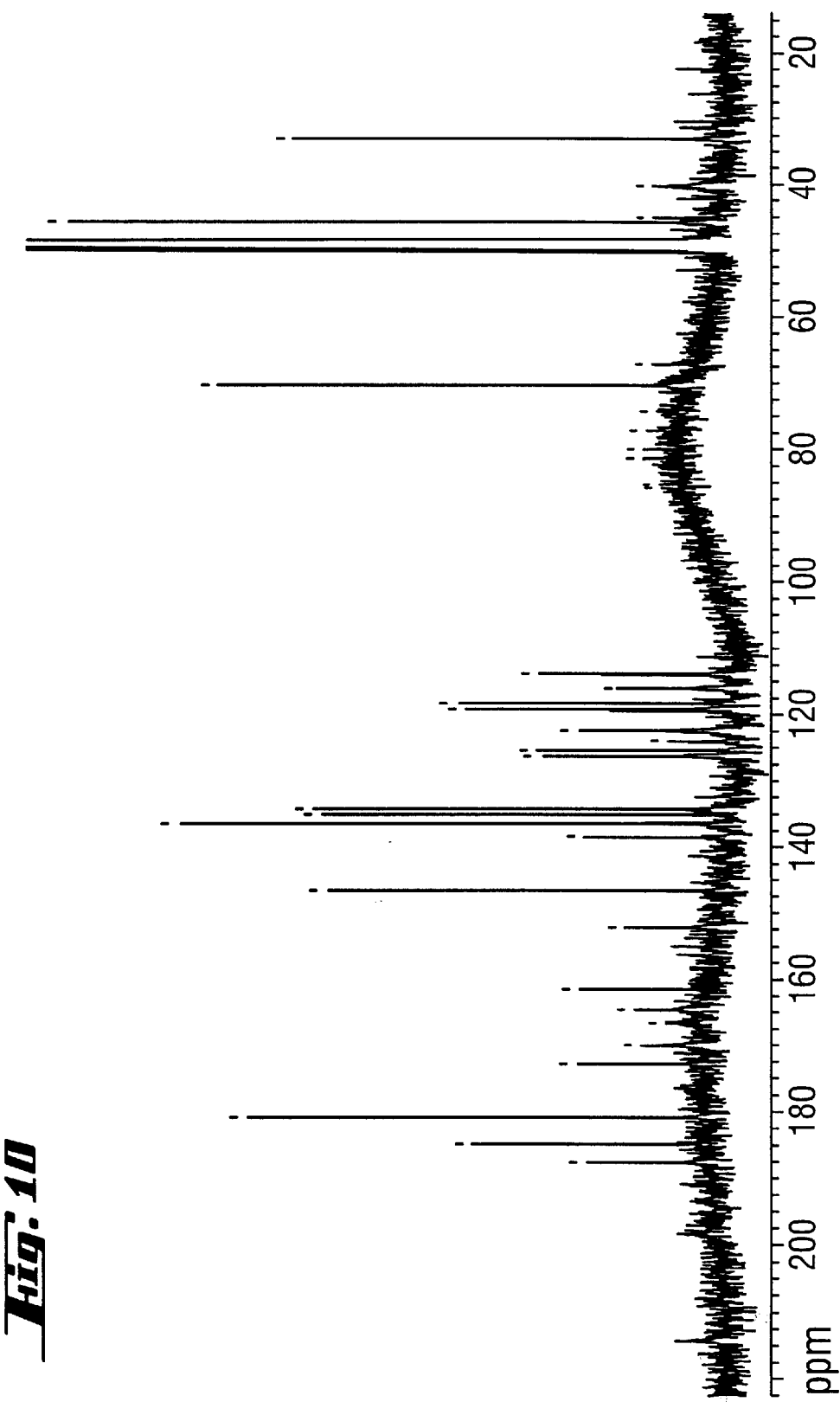
FIG. 10 shows the $^{13}C$ NMR spectrum of Mumbaistatin at 150 MHz in $d_4$-MeOH at 27° C.

| | Mumbaistatin | L970860 |
|---|---|---|
| $[\alpha]_D$ | −50.0° (c 0.024, MeOH) | −45.0° (c 0.02, MeOH) |
| High Pressure Liquid Chromatography (HPLC) | Retention Time: 10.83 min FIG. 1 of the drawings | Retention Time: 13.08 min FIG. 4 of the drawings |
| ESI-MS (Electrospray Ionization Mass) | 547 (M-H)⁻ | 529 (M-H)⁻ |
| Molecular formula | $C_{28}H_{20}O_{12}$ | $C_{28}H_{18}O_{11}$ |
| UV | FIG. 2 of the drawings | FIG. 5 of the drawings |
| IR (KBr) | FIG. 3 of the drawings | FIG. 6 of the drawings |
| $^1$H NMR | FIG. 9 of the drawings (600 MHz, $D_4$-MeOH, 27° C.) | FIG. 7 of the drawings (300 MHz, $D_6$-DMSO) |
| $^{13}$C NMR | FIG. 10 of the drawings (150 MHz, $D_4$-MeOH, 27° C.) | FIG. 8 of the drawings (75 MHz, $D_6$-DMSO) |

Pharmacological characterization of Mumbaistatin and the lactone L970860

Mumbaistatin potently inhibits the activity of rat liver microsomal glucose-6-phosphate translocase with an $IC_{50}$ of about 25 nM. In comparison, Mumbaistatin inhibits phosphatase activity in detergent-disrupted microsomes with an $IC_{50}$ of about >100 µM. Therefore, Mumbaistatin has a high degree of specificity for translocase. Furthermore, Mumbaistatin did not affect the activity of phosphate/pyrophosphate translocase. Mumbaistatin is a reversible and competitive inhibitor of glucose-6-phosphate translocase.

Mumbaistatin was further evaluated in isolated rat hepatocytes for its effect on glucose output. It inhibits both fructose-induced gluconeogenesis and glucagon-induced glycogenolysis with $IC_{50}$ values of about 0.3 µM and 0.6 µM, respectively.

L970860 inhibits the activity of rat liver microsomal glucose-6-phosphate translocase with an $IC_{50}$ of about 1.8 µM.

We claim:

1. Mumbaistatin, comprising a compound of molecular formula $C_{28}H_{20}O_{12}$, further defined by an $^1$H NMR spectrum as shown in FIG. 9, and a $^{13}$C NMR spectrum as shown in FIG. 10, or a pharmaceutically acceptable salt, ester, or ether of said compound.

2. A process for the production of Mumbaistatin or a salt, ester, or ether of said compound as claimed in claim 1, comprising cultivating Streptomyces species under aerobic conditions in a nutrient medium containing sources of carbon and nitrogen, followed by providing said compound, or salt, ester, or ether of said compound, by isolating said compound, salt, ester, or ether thereof from said Streptomyces or nutrient medium.

3. The method of claim 2, wherein the method further comprises purifying by gel permeation chromatography followed by reverse phase chromatography.

4. A pharmaceutical composition, comprising an effective amount of Mumbaistatin or a pharmaceutically acceptable salt, ester, or ether of said compound as claimed in claim 1, and at least one pharmaceutically acceptable carrier.

5. A method for inhibiting glucose-6-phosphate translocase, comprising administering to a host in need thereof an effective amount of Mumbaistatin or a pharmaceutically acceptable salt, ester, or ether of said compound as claimed in claim 1.

6. A method for treating diabetes mellitus, comprising administering to a host in need thereof an effective amount of Mumbaistatin or a pharmaceutically acceptable salt, ester, or ether of said compound as claimed in claim 1.

7. Mumbaistatin, comprising a compound of molecular formula $C_{28}H_{20}O_{12}$, or a pharmaceutically acceptable salt, ester, or ether thereof, obtained by the process of cultivating Streptomyces species under aerobic conditions in a nutrient medium containing sources of carbon and nitrogen, followed by isolating said compound or salt, ester, or ether of said compound.

8. The compound of claim 7, wherein the process further comprises purifying said compound of salt, ester or ether thereof.

9. A lactone L980860, comprising a compound of the molecular formula $C_{28}H_{18}O_{11}$, further defined by a $^1$H NMR spectrum as shown in FIG. 7, and a $^{13}$C NMR spectrum as shown in FIG. 8, or a pharmaceutically acceptable salt, ester, or ether of said compound.

10. A pharmaceutical composition, comprising an effective amount of lactone L980860 or a pharmaceutically acceptable salt, ester, or ether of said compound as claimed in claim 9, and at least one pharmaceutically acceptable carrier.

11. A method for inhibiting glucose-6-phosphate translocase, comprising adding to said translocase an effective amount of lactone L980860 or a pharmaceutically acceptable salt, ester, or ether of said compound as claimed in claim 9.

12. A method for treating diabetes mellitus, comprising administering to a host in need thereof an effective amount of lactone L980860 or a pharmaceutically acceptable salt, ester, or ether of said compound as claimed in claim 9.

13. Isolated Streptomyces species.

\* \* \* \* \*